United States Patent
Gubbens

(10) Patent No.: US 7,560,691 B1
(45) Date of Patent: Jul. 14, 2009

(54) HIGH-RESOLUTION AUGER ELECTRON SPECTROMETER

(75) Inventor: Alexander J. Gubbens, Redwood City, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 259 days.

(21) Appl. No.: 11/716,891

(22) Filed: Mar. 12, 2007

Related U.S. Application Data

(60) Provisional application No. 60/881,417, filed on Jan. 19, 2007.

(51) Int. Cl.
*H01J 49/48* (2006.01)

(52) U.S. Cl. .................. 250/305; 250/306; 250/307; 250/310

(58) Field of Classification Search .............. 250/305, 250/306, 307, 310
See application file for complete search history.

(56) References Cited

U.S. PATENT DOCUMENTS

| | | | |
|---|---|---|---|
| 4,358,680 A | 11/1982 | Read | |
| 4,639,597 A | 1/1987 | Shiokawa | |
| 5,032,723 A * | 7/1991 | Kono | 250/305 |
| 5,231,287 A | 7/1993 | Sekine et al. | |
| 5,315,113 A * | 5/1994 | Larson et al. | 250/305 |
| 6,455,848 B1 * | 9/2002 | Krijn et al. | 250/310 |
| 6,462,332 B1 | 10/2002 | Trompenaars et al. | |
| 6,946,654 B2 * | 9/2005 | Gerlach et al. | 250/310 |
| 7,294,834 B2 * | 11/2007 | Khursheed | 250/310 |
| 7,335,894 B2 * | 2/2008 | Frosien et al. | 250/396 R |

* cited by examiner

*Primary Examiner*—Jack I Berman
(74) *Attorney, Agent, or Firm*—Okamoto & Benedicto LLP

(57) ABSTRACT

One embodiment relates to a high-resolution Auger electron spectrometer in a scanning electron beam apparatus. An electron source generates a primary electron beam, and an immersion objective lens is configured to focus the primary electron beam onto a surface of a target substrate. A Wien filter is configured within the immersion objective lens and to deflect and disperse secondary electrons from the surface. A position sensitive detector is configured to receive the secondary electrons so as to detect an Auger electron spectrum. A first electron-optical lens may be positioned after the Wien filter so as to transfer a minimal-dispersion plane to an aperture plane. A second electron-optical lens may be positioned after the aperture so as to transfer a virtual focused-spectrum plane to a detector plane. Other embodiments, aspects and features are also disclosed.

22 Claims, 3 Drawing Sheets

HIGH-RESOLUTION AUGER ELECTRON SPECTROMETER

CROSS-REFERENCE TO RELATED APPLICATION

The present application claims the benefit of U.S. Provisional Patent Application No. 60/881,417, entitled "High-Resolution Auger Electron Spectrometer", filed Jan. 19, 2007, by inventor Alexander J. Gubbens, the disclosure of which is hereby incorporated by reference in its entirety.

BACKGROUND OF THE INVENTION

1. Field of the Invention

The present disclosure relates to Auger electron spectrometry and to electron beam apparatus.

2. Description of the Background Art

When an electron is emitted from a core level of an atom, leaving a vacancy, an electron from a higher energy level may fall into the lower-energy-level vacancy. This results in a release of energy either in the form of an emitted photon or by ejecting another electron. Electrons ejected in this manner are called Auger electrons.

Conventional Auger electron spectrometers include the hemispherical analyzer, the cylindrical mirror analyzer, and the hyperbolic field analyzer. The hemispherical analyzer and the cylindrical mirror analyzer are serial spectrometers where the spectrometer is scanned in order to collect a complete spectrum in a serial fashion. The hyperbolic field analyzer is an example of a parallel spectrometer where a complete spectrum is acquired in parallel fashion.

Auger electron spectrometers traditionally are incorporated into only non-immersion type scanning electron microscopes (SEMs). In such SEMs, the magnetic and/or electrostatic focusing fields are fully contained or nearly fully contained in the objective lens, and the sample is placed in a field-free or nearly field-free region below the lens. In such a spectrometer, the Auger electrons travel in substantially straight lines from the sample, and the spectrometer's collection efficiency is determined largely by the solid angle of the spectrometer's entrance aperture and the spectrometer's take-off angle with respect to the sample surface.

SUMMARY

One embodiment relates to a high-resolution Auger electron spectrometer in a scanning electron beam apparatus. An electron source generates a primary electron beam, and an immersion objective lens is configured to focus the primary electron beam onto a surface of a target substrate. A Wien filter is configured within the immersion objective lens and to deflect and disperse secondary electrons from the surface. A position sensitive detector is configured to receive the secondary electrons so as to detect an Auger electron spectrum. A first electron-optical lens may be positioned after the Wien filter so as to transfer a minimal-dispersion plane to an aperture plane. A second electron-optical lens may be positioned after the aperture so as to transfer a virtual focused-spectrum plane to a detector plane. Other embodiments, aspects and features are also disclosed.

Other embodiments, aspects and features are also disclosed.

DETAILED DESCRIPTION

There is an increasing need for high-resolution scanning electron microscopes (SEMs) in all areas of development and manufacture of micro-electronic and opto-electronic components. High-resolution scanning electron microscopes are useful so as to visually evaluate sub-micrometer structures. High-resolution SEMs may be used to identify deviations from standard patterns and to acquire and evaluate topographical data such as heights, widths or angles of inclination.

Unfortunately, conventional scanning electron microscopes do not have the required resolution of a few nanometers unless very high landing energies above about 10 kiloelectronVolts (keV) are used which may cause resist structures and integrated circuits to be damaged and non-conductive or high resistant specimens to be disadvantageously charged.

Low-Voltage SEMs with Immersion Objective Lenses

Low-voltage SEMs avoid the above-discussed problem of damaging specimens which is problematic in higher-voltage SEMs. It is advantageous to use an immersion objective lens in a low-voltage SEM because immersion objective lenses tend to have superior spatial resolution performance. Immersion objective lenses immerse the sample in a magnetic and/or decelerating electrostatic field.

Figure 1:
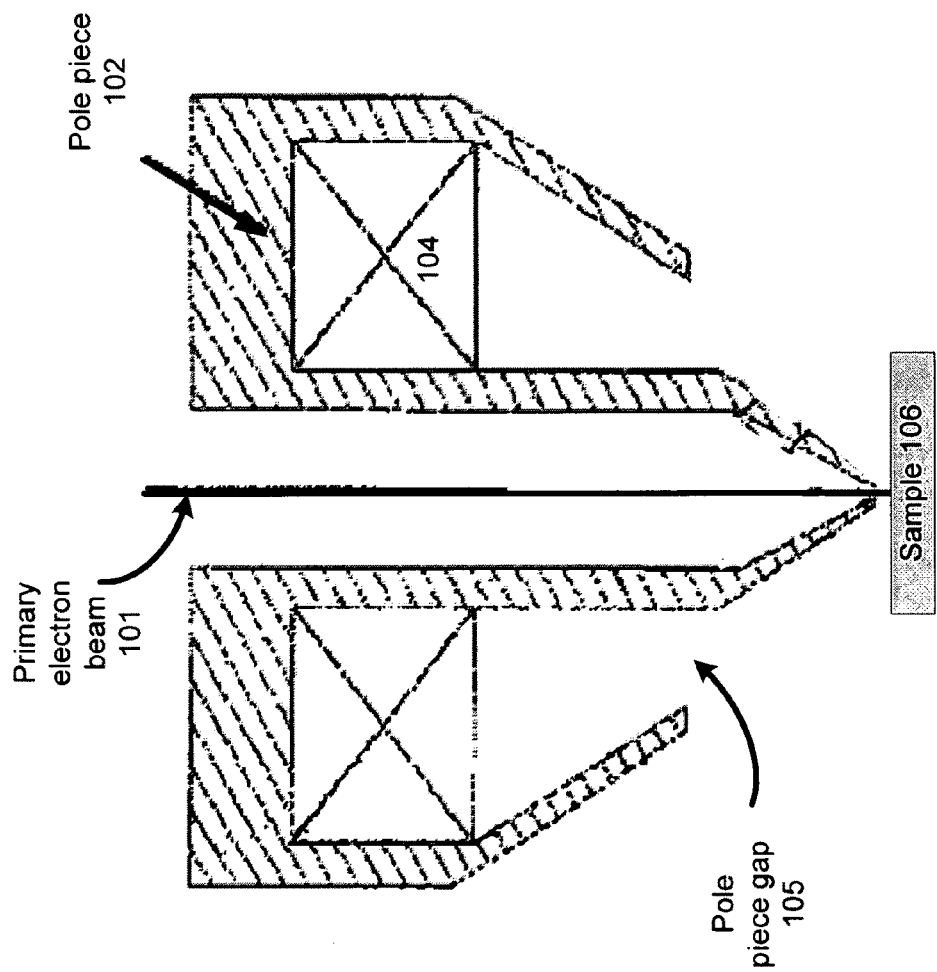
FIG. 1 is a cross-sectional diagram depicting a magnetic immersion objective lens for a scanning electron microscope.

FIG. 1 is a cross-sectional diagram depicting a magnetic immersion objective lens 100 for a scanning electron microscope. As shown, a primary electron beam 101 travels down an optical axis and through the objective lens 100 to become focused upon the surface of a target substrate. A magnetic pole piece 102 of the objective lens 100 is configured about the optical axis, with a gap 105 extending away from the optical axis. The pole piece 102 is configured about an electromagnetic device 104 so as to generate a magnetic field which immerses the target substrate. The pole piece 102 is further configured at a high voltage potential.

Incompatibility of Immersion Lenses with Conventional Auger Electron Spectrometry Because immersion lenses immerse the sample in a magnetic field and/or a decelerating electrostatic field, there is no field-free or nearly field-free region below the lens. As such, the Auger electrons cannot travel in substantially straight lines from the sample to an Auger spectrometer located outside the SEM column. Because of this, Auger spectrometry is typically performed with non-immersion lenses, and in the case of low voltage operation this unfortunately, limits the Auger spectrometry to lower spatial resolutions.

High-Resolution Auger Electron Spectrometer

The present disclosure enables a high-resolution Auger electron spectrometer. This is accomplished by incorporating the Auger spectrometer functionality into an immersion-type SEM in a way that does not interfere with or reduce the high-resolution performance of the SEM. An SEM configured in accordance with an embodiment of the invention may be used not only for high-resolution defect location and classification, but also for elemental analysis at a high spatial resolution (for example, at a nanometer level resolution).

Figure 2:
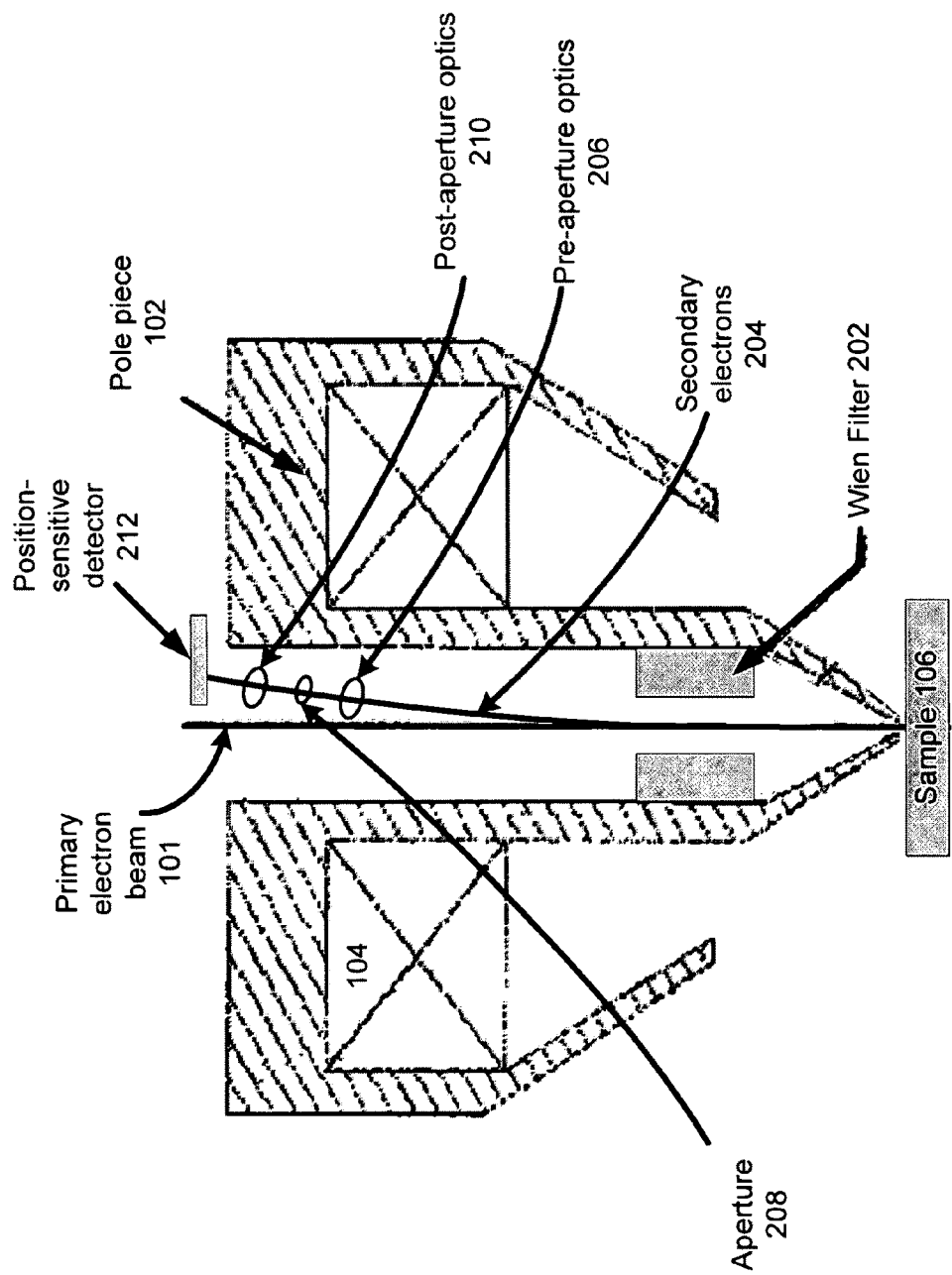
FIG. 2 is a schematic diagram of an immersion objective lens having additional components for high-resolution electron spectrometry in accordance with an embodiment of the invention.

FIG. 2 is a schematic diagram of an immersion objective lens system 200 having additional components for high-resolution Auger electron spectrometry in accordance with an embodiment of the invention. The additional components include a Wien filter 202, electron-optical lenses 206 and 210, an aperture 208, and a position-sensitive detector 212.

As shown in FIG. 2, secondary electrons (including Auger electrons) 204 are emitted from the sample 106 (for example, a manufactured semiconductor wafer, or other sample). These secondary electrons 204 spiral along the magnetic flux lines up the bore of the lens. Although in the strictest sense secondary electron means those electrons emitted from the sample with and energy equal to or less than 50 eV of energy, here secondary electrons cover all emitted electrons, including secondary, backscattered and Auger electrons.

In accordance with an embodiment of the invention, a Wien filter 202 located in the objective lens deflects the secondary electrons 204 off-axis (i.e. off the optical axis of the column). The Wien filter 202 also introduces an energy dispersion in the deflected secondary electrons 204. In alternate embodiments, another type of deflection device besides a Wien filter may be utilized. Other types of deflection devices include, for example, electrostatic deflectors. However, a Wien filter advantageously does not disturb the primary electron beam.

In one implementation, the Wien filter 202 may deflect the secondary electrons by about 6 degrees off-axis, where other conditions include a 5 keV primary beam energy, a 3 keV landing energy, and no electrostatic field between the magnetic immersion objective lens and the sample (such as, for example, a semiconductor wafer). Such conditions may be accomplished by having the electron gun (not shown) at −5 kilovolts, and the objective lens and the sample at −2 kiloVolts. Advantageously, such conditions minimize charging on a sample by having little or no electrostatic field between the sample and the objective lens.

In further accordance with an embodiment of the invention, the deflected secondary electrons have their trajectories transformed by pre-aperture electron-optics 206. The pre-aperture electron optics 206 focuses a minimal-dispersion plane near the center of the Wien filter 202 to the plane of the aperture 208 (i.e. to the aperture plane). The purpose of the aperture is to limit the polar angles of the electrons in order to improve the final energy resolution in the Auger spectrum. In one implementation, the pre-aperture electron optics 206 may be implemented with one or more round lenses. The minimal-dispersion plane and the function of the aperture 208 are described further below in relation to FIG. 3.

In further accordance with an embodiment of the invention, after passing through the aperture, the secondary electrons have their trajectories transformed by post-aperture electron-optics 210. The post-aperture electron optics 210 transfers a virtual focused-spectrum plane below the Wien filter 202 to the plane of the position-sensitive detector 212 (i.e. to the detector plane). The position-sensitive detector 212 may comprise a scintillator in combination with any multichannel detector suitable for spectroscopy, for example, charge coupled device (CCD) arrays, CMOS sensors, photodiode arrays and the like. In one implementation, the post-aperture electron optics 210 may be implemented with quadrupole lenses, preferably with separate control of x and y magnifications. The virtual focused-spectrum plane is described further below in relation to FIG. 4.

Figure 3:
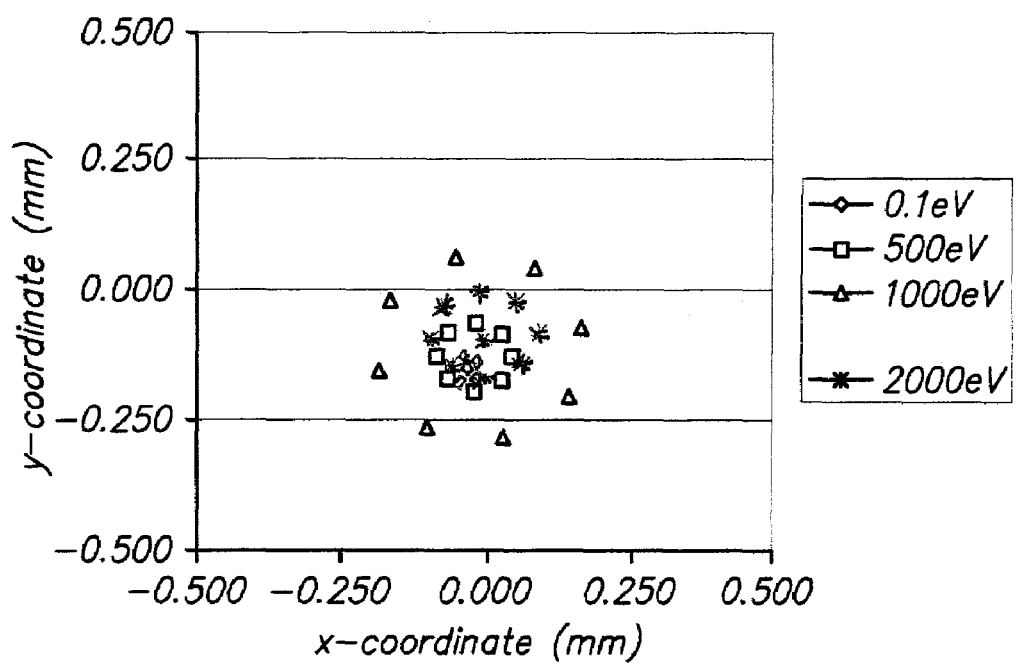
FIG. 3 is a graph showing the small or negligible energy dispersion at a plane near the middle of the Wien filter which may be mapped onto an aperture plane in accordance with an embodiment of the invention.

FIG. 3 is a graph showing the small or negligible energy dispersion at a minimal-dispersion plane near the middle of the Wien filter 202 which may be mapped onto the aperture plane in accordance with an embodiment of the invention. The graph in FIG. 3 is generated by a simulation which extrapolates back Auger electron ray traces through the Wien filter 202 to the minimal-dispersion plane at the middle of the Wien filter 202. The conditions for the simulation included a 5 keV primary beam energy, a 3 keV landing energy, and no electrostatic field between the magnetic immersion objective lens and the wafer sample.

Shown in FIG. 3 are circular patterns corresponding to Auger electrons at different energies emitted from a sample wafer at a polar angle of one degree and azimuthal angles ranging from 0 degrees to 360 degrees. As seen by the locations of the center of the circular patterns, the energy dispersion is small (near zero) at the minimal-dispersion plane.

The varying radii of the circular patterns indicates that the aperture 208 limits Auger electrons of different energies to different polar angles. This means that the collection efficiency of the high-resolution Auger spectrometer will vary across the energy spectrum. In accordance with an embodiment of the invention, this variation may be characterized and divided out prior to display and analysis of the Auger electron spectra.

Although an aperture may be placed, in theory, at this minimal-dispersion plane in the middle of the Wien filter 202, doing so would disadvantageously interfere with the functioning of the Wien filter as well as the primary electron beam and with the secondary electrons in a normal imaging mode. Hence, in accordance with an embodiment of the invention, the pre-aperture electron optics 206 is positioned and configured to transfer this minimal-dispersion plane to an aperture plane outside the Wien filter 202 (see aperture 208 in FIG. 2).

Figure 4:
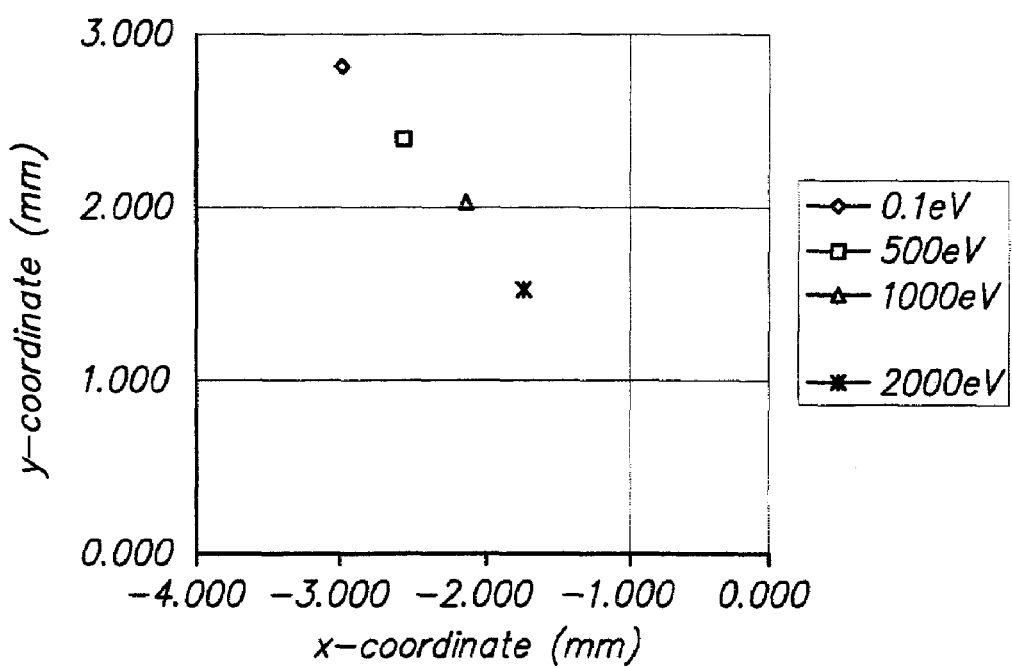
FIG. 4 is graph showing energy dispersion at a plane below a Wien filter which may be mapped onto a detector plane in accordance with an embodiment of the invention.

FIG. 4 is graph showing energy dispersion at a focused-spectrum plane below the Wien filter 202 which may be mapped onto the detector plane in accordance with an embodiment of the invention. The graph in FIG. 4 is also generated by a simulation. Here, the simulation extrapolates back Auger electron ray traces through the Wien filter 202 to a virtual focused-spectrum plane below the Wien filter 202. The conditions for the simulation are the same as those used to generate FIG. 3.

Shown in FIG. 4 are positions of the Auger electrons where the positions are dispersed depending on the energy of the Auger electrons. As seen, the dispersion is approximately along a line, though the magnitude of the dispersion has a non-linear dependence on energy.

In accordance with an embodiment of the invention, the post-aperture electron optics 210 is positioned and configured to transfer the virtual focused-spectrum plane to the detector plane (see position-sensitive detector 212 in FIG. 2). This function likely necessitates the separate control of x and y magnification. Hence, separate x and y quadrupole electron lenses may be used optionally in combination with rotationally symmetric electron lenses.

In accordance with an embodiment of the invention, because the magnitude of the dispersion is non-linear in relation to energy, this non-linearity would be characterized and transformation of the data would be made to properly stretch out the spectrum prior to display and analysis.

CONCLUSION

The present application discloses a technique for incorporating a fast, high-resolution Auger spectrometer into a high-resolution, low voltage, immersion lens SEM. Simulations generated by applicants show that such a spectrometer design provides an energy resolution ranging from about 1 eV at low Auger energies to about 10 eV at 2 keV Auger energy for a net collection efficiency of about 0.1%. Because the collection efficiency varies approximately linearly with energy resolution, a 2 times lower energy resolution may be traded off for a 4 times higher collection efficiency, for example.

In accordance with one embodiment, the Wien filter 220 may be operated in two settings. In one setting, the Wien filter 220 may deflect the secondary electrons in one direction towards a conventional secondary electron detector of the SEM. In the other setting, the Wien filter 220 may deflect the secondary electrons in an opposite or a different direction towards the Auger spectrometer. In accordance with an alternate embodiment, the function of the conventional secondary detector may be incorporated into the Auger spectrometer, such that only one operational setting for the Wien filter is needed.

The above-described diagrams are not necessarily to scale and are intended be illustrative and not limiting to a particular implementation. Specific dimensions, geometries, and lens currents of the immersion objective lens will vary and depend on each implementation.

The above-described invention may be used in an automatic inspection system and applied to the inspection of wafers, X-ray masks and similar substrates in a production environment. While it is expected that the predominant use of the invention will be for the inspection of wafers, optical masks, X-ray masks, electron-beam-proximity masks and stencil masks, the techniques disclosed here may be applicable to the high speed electron beam imaging of any material (including perhaps biological samples).

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A high-resolution Auger electron spectrometer in a scanning electron beam apparatus, the apparatus comprising:
   an electron source for generating a primary electron beam;
   an immersion objective lens configured to focus the primary electron beam onto a surface of a target substrate;
   a Wien filter configured within the immersion objective lens and to deflect and disperse secondary electrons from the surface; and
   a position sensitive detector configured to receive the secondary electrons so as to detect an Auger electron spectrum.

2. The apparatus of claim 1, wherein the immersion objective lens comprises a magnetic lens which generates a magnetic field at the target substrate.

3. The apparatus of claim 2, wherein the immersion objective lens is configured so as to not generate an electrostatic field at the target substrate.

4. The apparatus of claim 1, wherein the magnetic lens comprises a pole piece, and wherein the Wien filter is positioned within a bore of the pole piece.

5. The apparatus of claim 1, further comprising:
   a first electron-optical lens positioned after the Wien filter along a trajectory path of the secondary electrons; and
   an aperture positioned after the first electron-optical lens along the trajectory path of the secondary electrons.

6. The apparatus of claim 5, wherein the first electron-optical lens is configured to transfer a minimal-dispersion plane within the Wien filter to a plane of the aperture.

7. The apparatus of claim 6, wherein the first electron-optical lens comprises a round lens.

8. The apparatus of claim 5, further comprising a second electron-optical lens positioned after the aperture along the trajectory path of the secondary electrons.

9. The apparatus of claim 8, wherein the second electron-optical lens is configured to transfer a virtual focused-spectrum plane to a plane of the position-sensitive detector.

10. The apparatus of claim 9, wherein the second electron-optical lens comprises at least one quadrupole lens.

11. The apparatus of claim 9, wherein the second electron-optical lens comprises at least two quadrupole lenses, where the quadrupole lenses are configured to separately control magnification in two independent dimensions.

12. A method of performing high-resolution Auger electron spectrometry, the method comprising:
   generating a primary electron beam;
   using an immersion objective lens to focus the primary electron beam onto a surface of a target substrate;
   using a Wien filter configured within the immersion objective lens to deflect and disperse secondary electrons from the surface; and
   using a position sensitive detector to receive the secondary electrons so as to detect an Auger electron spectrum.

13. The method of claim 12, wherein the immersion objective lens comprises a magnetic lens which generates a magnetic field at the target substrate.

14. The method of claim 13, wherein the immersion objective lens is configured so as to not generate an electrostatic field at the target substrate.

15. The method of claim 12, wherein the magnetic lens comprises a pole piece, and wherein the Wien filter is positioned within a bore of the pole piece.

16. The method of claim 12, further comprising:
   using a first electron-optical lens positioned after the Wien filter along a trajectory path of the secondary electrons; and
   using an aperture positioned after the first electron-optical lens along the trajectory path of the secondary electrons.

17. The method of claim 16, wherein the first electron-optical lens is used to transfer a minimal-dispersion plane within the Wien filter to a plane of the aperture.

18. The method of claim 17, wherein the first electron-optical lens comprises a round lens.

19. The apparatus of claim 16, further comprising:
   using a second electron-optical lens positioned after the aperture along the trajectory path of the secondary electrons.

20. The method of claim 19, wherein the second electron-optical lens is used to transfer a virtual focused-spectrum plane to a plane of the position-sensitive detector.

21. The method of claim 20, wherein the second electron-optical lens comprises at least one quadrupole lens.

22. The method of claim 20, wherein the second electron-optical lens comprises at least two quadrupole lenses, where the quadrupole lenses are configured to separately control magnification in two independent dimensions.

* * * * *